United States Patent
Itsuji (10) Patent No.: US 8,263,937 B2
(45) Date of Patent: Sep. 11, 2012

(54) APPARATUS AND METHOD FOR ACQUIRING TIME WAVEFORM OF TERAHERTZ WAVES

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 357 days.

(21) Appl. No.: 12/788,576

(22) Filed: May 27, 2010

(65) Prior Publication Data

US 2010/0308223 A1 Dec. 9, 2010

(30) Foreign Application Priority Data

Jun. 5, 2009 (JP) .................................. 2009-135631

(51) Int. Cl.
*G01J 5/02* (2006.01)

(52) U.S. Cl. ...................................... 250/340

(58) Field of Classification Search ................... 250/340
See application file for complete search history.

(56) References Cited

U.S. PATENT DOCUMENTS

2010/0090112 A1* 4/2010 Kawada et al. ............ 250/338.4

FOREIGN PATENT DOCUMENTS

JP 2008-014815 A 1/2008

* cited by examiner

*Primary Examiner* — David Porta
*Assistant Examiner* — Hugh H Maupin
(74) *Attorney, Agent, or Firm* — Canon USA, Inc., IP Division (57) ABSTRACT

A method for acquiring an accurate time waveform of terahertz waves includes: acquiring a first time waveform by using a first delay portion with a first difference in length of the optical paths in the second delay portion, using a second delay portion to change the first difference in length of the optical paths to a second difference in length of the optical paths that is different from the first difference in length of the optical paths, acquiring a second time waveform by using the first delay portion with the second difference in length of the optical paths, adjusting the acquired first and second time waveforms in accordance with a predetermined differences in length of the optical paths based on the first and second differences in length of the optical paths, and averaging the first and second time waveforms according to the predetermined difference in length of the optical paths.

4 Claims, 9 Drawing Sheets

APPARATUS AND METHOD FOR ACQUIRING TIME WAVEFORM OF TERAHERTZ WAVES

BACKGROUND OF THE INVENTION

1. Field of the Invention

The present invention relates to apparatuses and methods for acquiring a time waveform of terahertz waves. The present invention particularly relates to a terahertz wave measuring system (which may be called a THz-TDS system or THz-time domain spectroscopy system) and method which measure terahertz waves in the time domain.

2. Description of the Related Art

Terahertz waves are electromagnetic waves that have a component in an arbitrary frequency band in the range from 0.03 THz to 30 THz. In such a frequency band, many distinct absorption bands are present due to the structures and/or states of various substances including biomolecules. The characteristic is used in examination technologies developed for nondestructive analysis or identification of a substance. It has been expected that terahertz waves would be applied to imaging technologies so as not to use X-rays, and applied to high-speed communication technologies and the like.

The time waveform of terahertz waves is subpicosecond pulse shape in many cases. Since such pulses are difficult to acquire in real time, a THz-TDS system performs sampling measurement using excitation light having a pulse width of the femtosecond order. The sampling can be implemented by adjusting the difference between times taken for the excitation light beams to reach a generating portion which generates terahertz waves and to reach a detecting portion which detects the waves. For example, a stage (will also be called delay optical portion) may be provided in a propagation path of the excitation light. The stage has a folding optical system, and the time difference may be acquired by adjusting the amount of folding. The generating portion or detecting portion may sometimes be a photoconductor with an antenna pattern having a microgap in a semiconductor film. The following descriptions assume that the generating portion or detecting portion is such a photoconductor.

In recent years, there have been pointed out the influences of swinging of the stage used as the delay optical portion with the improvements in measurement sensitivity of the THz-TDS system. (Refer to Japanese Patent Laid-Open No. 2008-014815). When the stage used as the delay optical portion swings, the optical axis of the excitation light sways. This as a result changes the quantity of light per unit area radiated to the microgap in the photoconductor, which may deteriorate the SN ratio of terahertz signal.

The stage being the delay optical portion as described above may sometimes be a linear-motion stage which moves several tens of millimeters. The linear-motion stage may sometimes be a combination of a stepping motor and a micro ball screw to move a table. Since such a stage mechanically moves a table, a surface of the table may be displaced from a base plane, on which the stage is placed, due to non-uniformity of the thread pitch of the ball screw and the like. Under certain environmental conditions such as those of the ambient atmosphere around the delay optical portion or under certain installation condition such as location of the delay optical portion, the surface of the table may also be displaced from the base plane. Displacement may be caused by distortion of the housing and/or member supporting the delay optical portion and/or caused by the stage vibrating at a frequency inherent to the place where the stage is located. When the displacement due to the movement of the table causes periodic swinging of the delay optical portion, the optical axis of the excitation light periodically sways. Thus, a periodical signal component is superposed on the time waveform of terahertz waves. Performing a Fourier transform on the time waveform results in a spectrum of the terahertz wave detected by the detecting portion and a pseudospectrum due to the swinging of the delay optical portion. For example, the superposition of a frequency component of a swing being several hundred Hz on a time waveform of terahertz waves may result in a pseudospectrum around 4 to 6 THz. This reduces the measurement band width for a measuring apparatus and may lower the analysis performance.

SUMMARY OF THE INVENTION

Accordingly, the present invention provides a method which may suppress an influence of a mechanical movement of a delay portion and acquire a time waveform of terahertz waves.

A method for acquiring an accurate time waveform of terahertz waves according to an aspect of the present invention in an apparatus including a generating portion which generates terahertz waves, a detecting portion which detects the terahertz waves, a first delay portion which changes the difference in length of the optical paths of excitation light beams radiated to the generating portion and the detecting portion, and a second delay portion which changes the difference between times taken for the excitation light beams to reach the generating portion and to reach the detecting portion includes acquiring a first time waveform by using the first delay portion with a first difference in length of the optical paths, using the second delay portion to change the first difference in length of the optical paths to a second difference in length of the optical paths which is different from the first difference in length of the optical paths, acquiring a second time waveform by using the first delay portion with the second difference in length of the optical paths, adjusting the acquired first and second time waveforms in accordance with a predetermined difference in length of the optical paths based on the first and second difference in length of the optical paths, and averaging the first and second time waveforms according to the predetermined difference in length of the optical paths to supply the accurate time waveform.

Further aspects of the present invention will become apparent from the following description of exemplary embodiments with reference to the attached drawings.

DESCRIPTION OF THE EMBODIMENTS

Embodiments of the present invention will be described below. An important feature in an apparatus and method for acquiring a time waveform of terahertz waves of the present invention is as follows. A plurality of measured time waveforms of terahertz waves are adjusted in accordance with a difference in optical length predetermined from a plurality of differences in optical length in a second delay portion, and the plurality of time waveforms according to the predetermined difference in optical length are averaged.

On the basis of the feature, a fundamental embodiment of the art of the present invention for acquiring a time waveform of terahertz waves has the configuration as follows. A method of according to an embodiment of the present invention is a method for acquiring a time waveform of terahertz waves in an apparatus including a first delay portion and includes the following first to fifth steps. The first delay portion here adjusts the difference between times taken for excitation light beams to reach a generating portion which generates terahertz waves and to reach a detecting portion which detects the terahertz waves in accordance with the difference in length of the optical paths where the excitation light beams propagate. In the first step, a movement of the first delay portion is used to measure a first time waveform at a first state where the difference in length of the optical paths is set to a first difference in length of the optical paths (will be called a first value). In the second step, the first state is shifted to a second state where the difference in length of the optical paths is set to a second difference in length of the optical paths (will be called a second value) that is different from the first value. In the third step, at the second state, a movement of the first delay portion is used to measure a second time waveform. In the fourth step, data sequences on the first and second terahertz wave time waveforms are converted to data sequences at a predetermined position of the first delay portion at a reference state where the difference in length of the optical paths has a reference value. In other words, a plurality of differences in optical path in the second delay portion which changes the difference in length of the optical paths are adjusted in accordance with a predetermined difference in length of the optical paths. In the fifth step, the time waveforms acquired by the fourth step are averaged. An apparatus according to an embodiment of the present invention for acquiring a time waveform of terahertz waves includes a first delay portion, a second delay portion, and a processing portion. The first delay portion performs a predetermined movement to change a difference between times taken for excitation light beams to reach a generating portion which generates terahertz waves and to reach a detecting portion which detects the terahertz waves in accordance with the change in difference in length of the optical paths where excitation light beams propagate. The second delay portion adjusts the difference in length of the optical paths at a state where the first delay portion performs the predetermined movement. The processing portion averages a plurality of time waveforms measured when the first delay portion performs the predetermined move at a plurality of states where the second delay portion adjusts the difference in length of the optical paths to different values. The processing portion converts data sequences on the plurality of time waveforms to a data sequence from a predetermined position of the first delay portion at a reference state where the difference in length of the optical paths has a reference value and averages the converted data sequences.

On the basis of the fundamental embodiment, the following specific embodiment can be implemented. At a state where the first delay portion performs a predetermined move, the difference in length of the optical paths can be set by the second delay portion. A terahertz wave acquisition technology may be used to radiate terahertz waves from the generating portion to a sample, detect the terahertz wave having passed through or reflected by the sample by the detecting portion and acquire information on the sample at a state where a signal having a predetermined frequency component in real time originating in the movement of the first delay portion is suppressed.

The first delay portion performs a predetermined movement from a predetermined origin position, which is a home position for time-waveform measurement, every time-waveform measurement. The first delay portion includes a movable section which mechanically moves. When the movable section is an optical system such as a folding mirror as in the example which will be described below, the first delay portion will be called a first delay optical portion. The second delay portion adjusts the difference in length of the optical paths of excitation light beams at the predetermined origin position of the predetermined movement by the first delay portion every time-waveform measurement. Thus, at positions involved in the predetermined movement, the differences in length of the optical paths produced by the first delay portion with adjustment using the second delay portion are displaced relative to the difference before the adjustment by the amount of adjustment. The second delay portion may include a movable section which mechanically moves or may change the time constants (of the index of refraction) in the optical paths where excitation light beams propagate under electrical control with electro-optic crystal, for example. In other words, the second delay portion may only be required to adjust the difference in length of the optical paths of the excitation light beams at the origin position of the first delay portion. When the second delay portion includes a movable section, as in the example which will be described below, and the movable section is an optical system such as a folding mirror, the second delay portion will be called a second delay optical portion. The "state" of the first state where the difference in length of the optical paths is set to a first value or the second state where it is set to a second value will be called a "position" such as a first position and a second position, as in the example which will be described below, if the difference in length of the optical paths is adjusted with the movement of the position of the movable section of the second delay portion including the movable section. The amount of adjustment by the second delay portion may be defined by a measurement position output portion in the example which will be described below. The amount of adjustment may be within the adjustment range for a difference in length of the optical paths of V*T including the value of the difference in length of the optical paths at the predetermined position in order to effectively suppress signals having a predetermined frequency component in real time originating in a movement of the first delay portion. In this case, V is a working velocity of the movement by the first delay portion, and T is a period of a predetermined frequency component in real time originating in the movement by the first delay portion.

[First Embodiment]

Next, the forms that can embody the spirit of the present invention will be described with reference to drawings. A first embodiment of a terahertz wave measuring apparatus illustrated FIG. 1A follows a basic configuration of a THz-TDS system and measures a time waveform of terahertz waves in the time domain. The part measuring a time waveform of terahertz waves includes a generating portion 101, a detecting portion 102, a first delay optical portion 103, a processing portion 106, a biasing portion 107, a current detecting portion 108, and a laser source 109. This embodiment further includes a second delay optical portion 104 and a measurement position output portion 105 in addition to the basic configuration in order to suppress a frequency component of a periodic swing originating in the first delay optical portion 103.

Figure 1A:
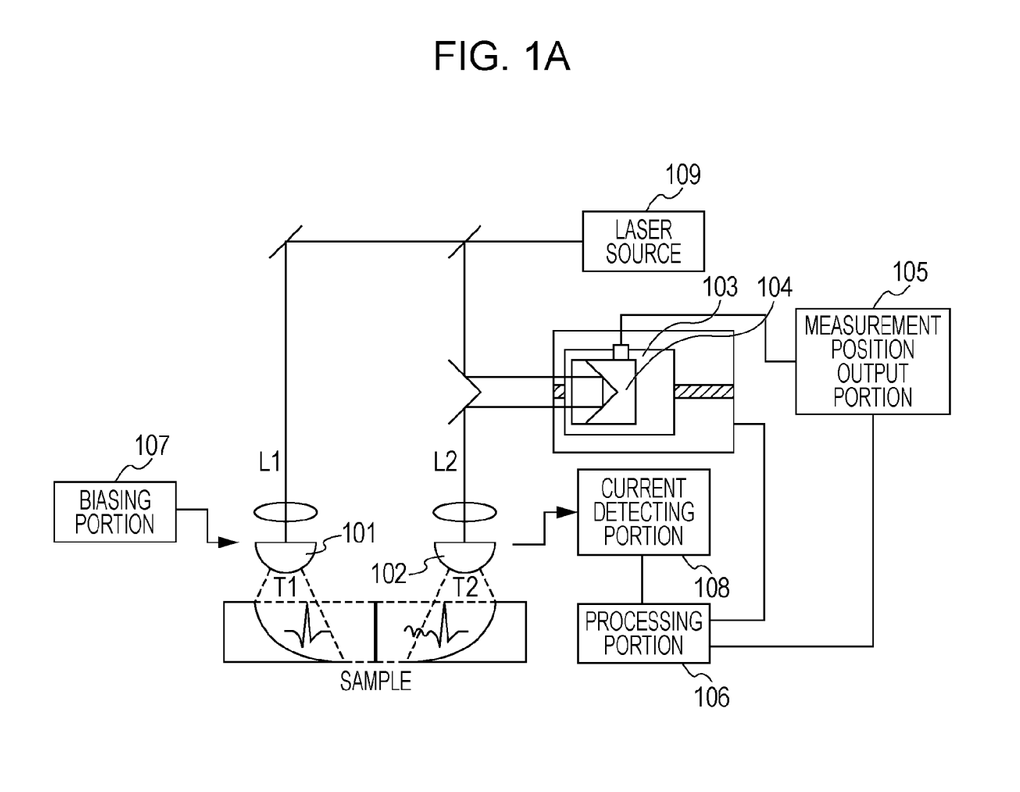
FIG. 1A is a schematic configuration diagram of a first embodiment of a terahertz wave measuring apparatus and method according to the present invention.

The generating portion 101 generates terahertz waves. The generating portion 101 may adopt a method using instantaneous carrying current or a method using interband transition of a carrier. The former method may generate terahertz waves by radiating laser light to a surface of a semiconductor or organic crystal or may apply an electric field to a photoconductor having an antenna pattern of metal electrodes on a semiconductor thin film and radiate laser light. A PIN diode is also applicable. The method using a gain structure may use a semiconductor quantum well structure. According to this embodiment, the first delay optical portion 103 is a photoconductor. The detecting portion 102 detects the electric field intensity of terahertz waves. The detecting portion 102 may detect the current corresponding to the electric field intensity with photoconductivity, may use an electro-optic effect to detect an electric field, or may use a magneto-optical effect to detect a magnetic field. In order to detect current with photoconductivity, a photoconductor is applicable. In order to detect an electric field by using an electro-optic effect, an orthogonal polarizer and electro-optic crystal may be used. In order to detect a magnetic field by using a magneto-optical effect, an orthogonal polarizer and magnet-optical crystal may be used. The terahertz waves entering to the detecting portion 102 may be focused on the detecting portion 102 to increase the intensity per unit area and increase the detection sensitivity. According to this embodiment, the second delay optical portion 104 is a photoconductor.

The laser source 109 outputs ultra-short pulse laser. The generating portion 101 and detecting portion 102 operate with the excitation of the carriers by the ultra-short pulse laser. As illustrated in FIG. 1A, the ultra-short pulse laser is divided into two optical paths L1 and L2. The ultra-short pulse laser (will be also called an excitation light beam L1) passing through the optical path L1 is input to the generating portion 101. The ultra-short pulse laser (will be also called an excitation light beam L2) passing through the optical path L2 is input through the first delay optical portion 103 to the detecting portion 102.

The first delay optical portion 103 adjusts the position for sampling a time waveform of terahertz waves in the detecting portion 102. More specifically, for example, the first delay optical portion 103 delays the timing of the input of the excitation light beam L2 to the detecting portion 102 relative to the input of the excitation light beam L1 to the generating portion 101. In order to adjust the time difference between the excitation light beams L1 and L2, the lengths of the optical paths where the excitation light beams propagate may be directly adjusted, or the effective optical path lengths may be adjusted. The former method uses a folding optical system and a movable section. The latter method changes time constants within the optical paths where the excitation light beams propagate. For example, optical crystal which changes its thickness may be put in and taken out to the optical paths by a mechanical movement mechanism. In any method used, the first delay optical portion 103 has a mechanical movable section. FIG. 1A illustrates one-segmented folding optical system and a linear-motion stage functioning as the movable section, for example. On the other hand, the second delay optical portion 104, which will be described below, may only be required to adjust the time difference between the excitation light beams L1 and L2 and may not typically have a mechanical movable section but may have any form. For example, the second delay optical portion 104 may change the voltage to be applied to the electro-optic crystal to change the time constant in the optical path where the electro-optic crystal is provided.

The biasing portion 107 supplies a bias for driving the generating portion 101. When the generating portion 101 is a photoconductor, the biasing portion 107 biases metal electrodes having an antenna pattern. More specifically, when the current detecting portion 108 includes a lock-in detection system, the bias supplied by the biasing portion 107 may be modulated with the frequency equivalent to that of a reference signal of the lock-in detection system. The current detecting portion 108 converts a current signal to a measurable voltage signal. When the detecting portion 102 is a photoconductor, the current detecting portion 108 converts the current signal output from the detecting portion 102 to a voltage signal. As described above, if the signal output from the detecting portion 102 is minute, the current detecting portion 108 may include a lock-in detection system. However, according to the present invention, the current detecting portion 108 may not be required but may be replaced in accordance with the signal from the detecting portion 102 by a device which can adjust the signal to a signal which is easily processable by the processing portion 106.

The processing portion 106 constructs a time waveform of terahertz waves. The processing portion 106 refers to the amount of adjustment (which is the amount of movement of the linear-motion stage according to this embodiment) by the first delay optical portion 103 and the output by the current detecting portion 108 and constructs a time waveform. The processing portion 106 may average a plurality of time waveforms to improve the SN ratio. In order to calculate a frequency spectrum here, the processing portion 106 performs Fourier transform on the time waveform. When the THz-TDS system is used as an analysis apparatus, the processing portion 106a calculates a change in time waveform upon radiation of terahertz waves to a sample arranged as illustrated in FIG. 1A. The processing portion 106 further monitors the relative positions of the radiated terahertz waves and a sample to visualize the sample. This configuration is generally known as that of a THz-TDS system.

As illustrated in FIG. 1A, an embodiment of the present invention includes the second delay optical portion 104 and the measurement position output portion 105 in order to suppress a frequency component of a swing originating in the first delay optical portion 103. This frequency component will also be expressed herein as a predetermined frequency component of a time waveform of terahertz waves.

The second delay optical portion 104 defines a position for measuring a time waveform of terahertz waves. Like the first delay optical portion 103, the second delay optical portion 104 adjusts the difference between times taken for the excitation light beams L1 and L2 to reach the generating portion 101 and to reach the detecting portion 102. More specifically, the first delay optical portion 103 adjusts the point of sampling on a time waveform of terahertz waves while the second delay optical portion 104 slightly changes the positions of sampling determined by the first delay optical portion 103 every measurement of a time waveform. More detail operations will be described below. The measurement position output portion 105 adjusts the amount of movement by the second delay optical portion 104 and outputs the amount of movement to the processing portion 106. The present apparatus repetitively measures terahertz waves and averages time waveforms of the terahertz waves. The measurement position output portion 105 adjusts the amount of movement by the second delay optical portion 104 every measurement of terahertz waves.

Next, operations by the present apparatus of this embodiment will be described. The present apparatus measures a time waveform of terahertz waves a plurality of numbers of time and averages the time waveforms. In FIG. 1A, the generating portion 101 irradiated with the excitation light beam L1 generates terahertz waves T1. When a sample is present in the propagation path of the terahertz waves, the terahertz waves T1 become terahertz waves T2 containing influences of absorption and/or scattering by the sample and enter to the detecting portion 102. The terahertz waves T2 incident on the detecting portion 102 are sampled and measured with the excitation light beam L2 having passed through the first delay optical portion 103. The point for sampling is adjusted by changing the difference in length of the optical paths where the excitation light beams L1 and L2 propagate in the first delay optical portion 103. The sampled signal is transmitted through the current detecting portion 108 to the processing portion 106 and is plotted along with the amount of adjustment of the first delay optical portion 103 to construct a time waveform. The operations up to this point are those by a general THz-TDS system. The present apparatus according to this embodiment adjusts the second delay optical portion 104 during a plurality of measurements of time waveforms to suppress signals of a predetermined frequency component (which is the sway of excitation light originating in the first delay optical portion 103). The operation will be described below.

Figure 1B:
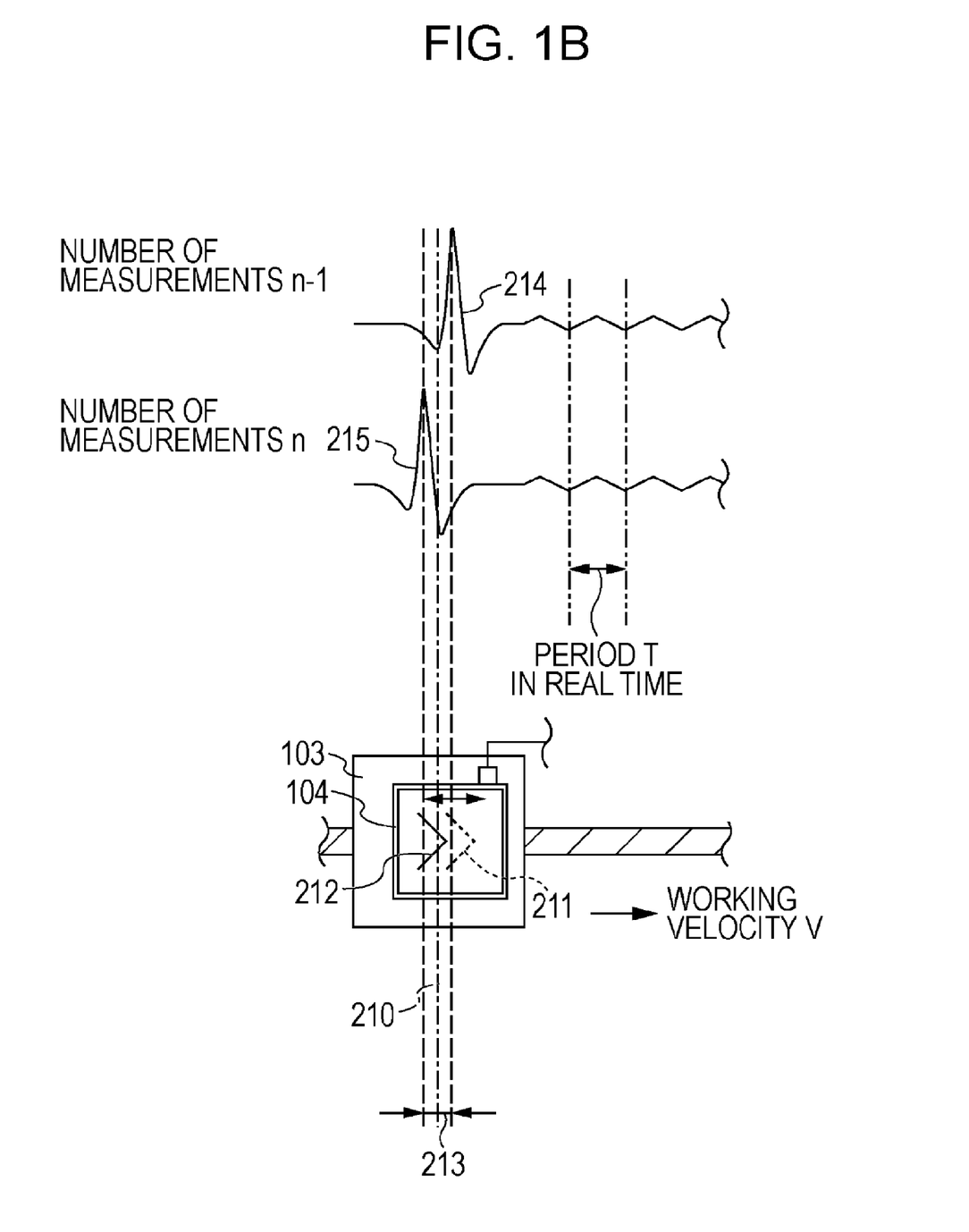
FIG. 1B illustrates operations by a first delay portion and second delay portion.

As illustrated in FIG. 1B, the second delay optical portion 104 is placed on a stage included in the first delay optical portion 103. A folding mirror included in the first delay optical portion 103 is placed on the second delay optical portion 104. The processing portion 106 in FIG. 1A defines the positions of the second delay optical portion 104 and first delay optical portion 103 and defines a reference position A 210 in FIG. 1B. The position A 210 may have a peak of a time waveform, for example. The processing portion 106 finally provides a time waveform of the terahertz waves at the position A 210. The measurement position output portion 105 adjusts the second delay optical portion 104 every measurement to change the position for measuring in a range including the position A 210. For example, referring to FIG. 1B, if the number of measurements is equal to n−1, the second delay optical portion 104 adjusts the folding mirror included in the first delay optical portion 103 to a first position 211. At this state, the first delay optical portion 103 is used to acquire a time waveform 214 of the first terahertz wave. If the number of measurements is equal to n, the second delay optical portion 104 adjusts the folding mirror to a second position 212 that is different from the first position 211. At this state, the first delay optical portion 103 is used to acquire a time waveform 215 of the second terahertz wave.

Comparing the time waveform 214 of the first terahertz wave and time waveform 215 of the second terahertz wave, the peaks of the terahertz wave pulses occur at different positions. However, there are no substantial changes in phase of the signal of the frequency component of a swing originating in the first delay optical portion 103. This is because the signal of the frequency component of a swing is fixed unless the driving start position or driving velocity (or the form of swinging of the first delay optical portion 103 of every measurement) of the stage of the first delay optical portion 103 is changed since the signal of the frequency component of the swing originates in the first delay optical portion 103. For convenience of illustration, FIG. 1B illustrates the signal of the predetermined frequency component independently of terahertz wave pulses. However, in practice, the signal of a predetermined frequency component is entirely superposed on the time waveform of terahertz waves.

Figure 2A:
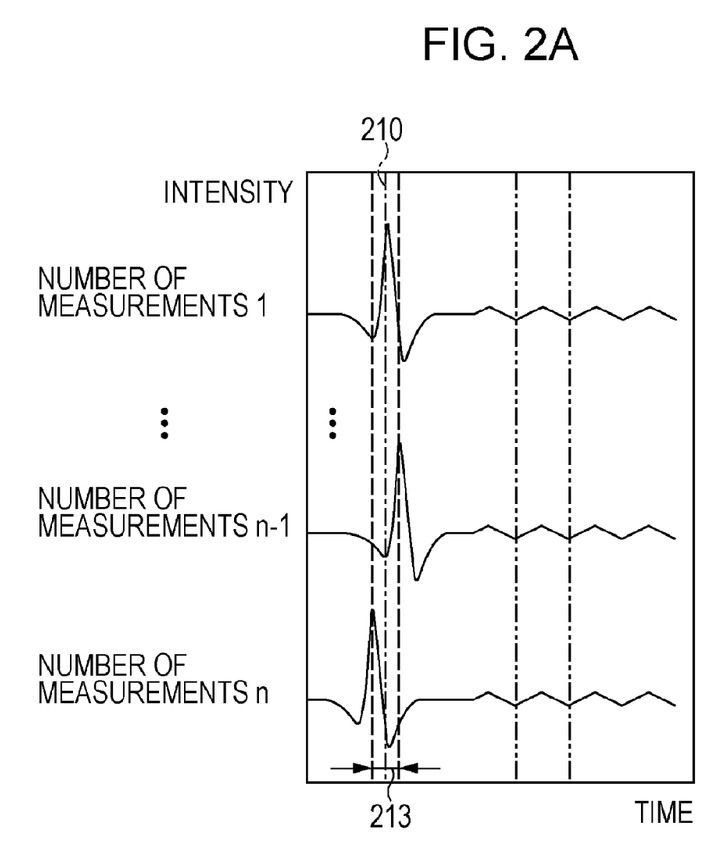
FIG. 2A illustrates the steps of processing a time waveform of terahertz waves.
Figure 2B:
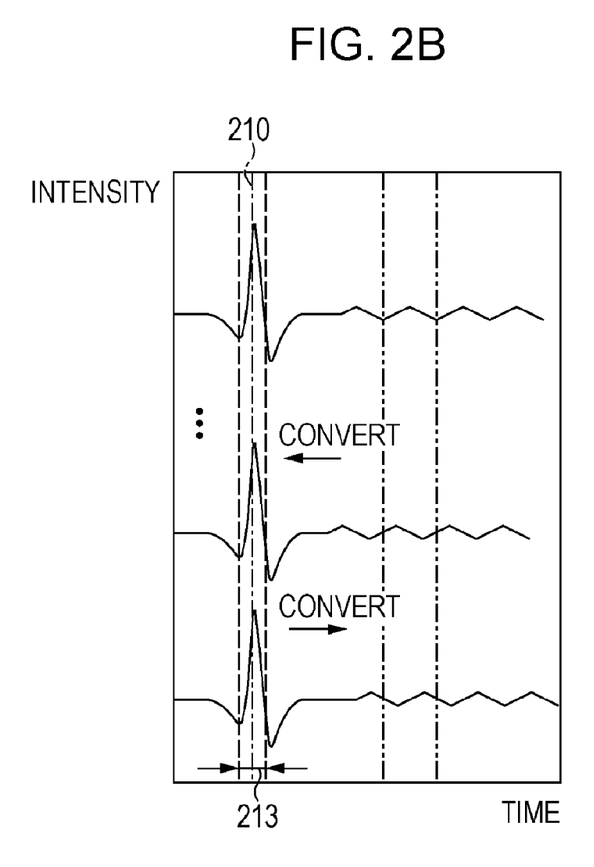
FIG. 2B illustrates the steps of processing a time waveform of terahertz waves.
Figure 2C:
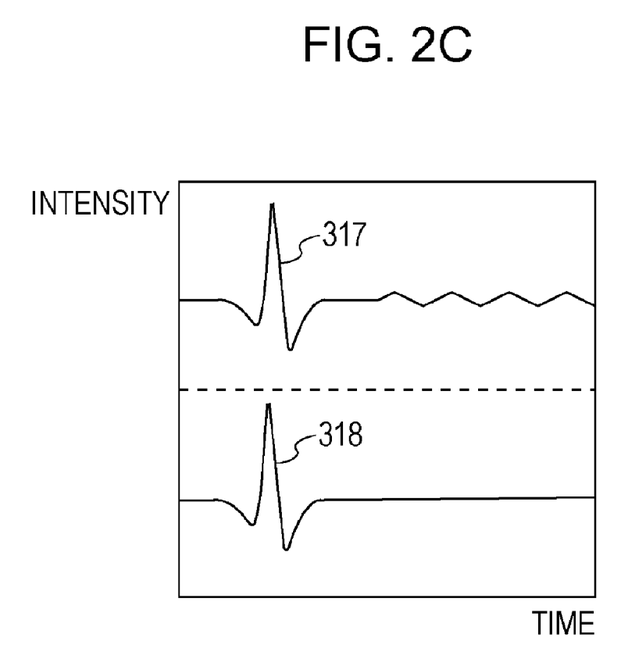
FIG. 2C illustrates the steps of processing a time waveform of terahertz waves.
Figure 2D:
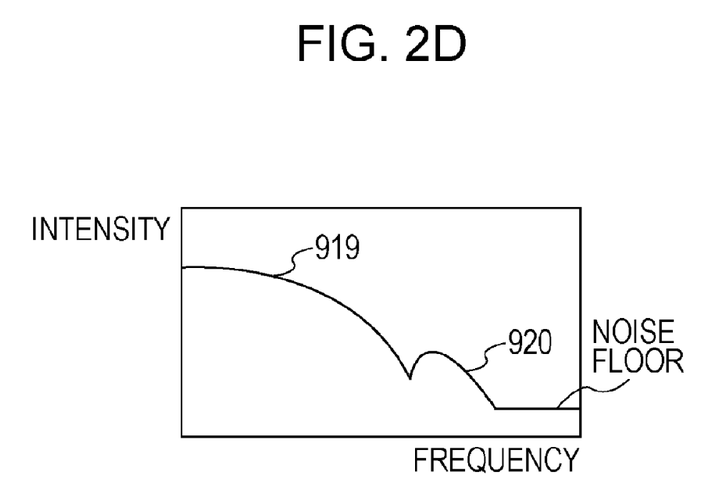
FIG. 2D illustrates a pseudospectrum due to swinging of a delay optical portion.

When the first delay optical portion 103 is moved at a velocity V of approximately 10 mm/s every measurement of a time waveform of terahertz waves, for example, the first delay optical portion 103 may often swing at a frequency of several thousand kHz in consideration of the form of the ball screw and so on. When a time waveform of terahertz waves is sampled every time when the first delay optical portion 103 moves several micrometers to several tens of micrometers, the sampling frequency is lower than the frequency of the swing. More specifically, because of the influence of the aliasing, the frequency component of the swing is converted to a signal at several hundred Hz. The conversion of the signal of the frequency component of a swing being several hundred Hz to a time waveform of terahertz waves results in a frequency component of approximately 5 THz. Although, (as illustrated in FIG. 2D), due to the swinging of the first delay optical portion 103, the conversion results in a pseudospectrum 920, the present invention can beneficially suppress the impact of the pseudospectrum unlike the prior art. The signal component (having a time axis defined by the velocity of movement by the first delay optical portion 103) before converted to a time waveform of terahertz waves is a signal component in real time herein. The adjustment range 213 for the difference in length of the optical paths by the second delay optical portion 104 may be V*T where the period of a frequency component in real time is T. Referring to FIG. 1B, since one-segmented folding optical system is used, the second delay optical portion 104 moves the folding optical system in the range of (½)*V*T.

The steps of processing a time waveform of the terahertz waves will be described. Changing the position for measuring by the second delay optical portion 104 every measurement constructs time waveforms having different peak positions of pulses as illustrated in FIG. 2A in the processing portion 106. The processing portion 106 adjusts the peak positions of the pulses to the position A 210 to average those time waveforms. More specifically, the time axes of the data sequences on the time waveforms of terahertz waves are moved such that the peak positions of pulses can be the position A 210. FIG. 2B illustrates the time waveforms after the conversion step on the data sequences. Referring to FIG. 2B, the time waveforms after the conversion step have the peak positions of pulses at the position A but have different phases of the frequency component of the swing originating in the first delay optical portion 103. Because of the difference in phase of the frequency component, when the waveforms are averaged, a time waveform 318 having the predetermined frequency component suppressed can be acquired instead of the time waveform 317 in the past on which the frequency component of the swing is superposed as illustrated in FIG. 2C.

Defining the adjustment range 213 for the difference in length of the optical paths to be adjusted by the second delay optical portion 104 to V*T, the change in phase of the frequency component of a swing can be within one wavelength. This can prevent the repetitive influences of the swinging (such as the occurrence of the first and second swinging waveforms at relatively the same positions). Thus, the frequency component of a swing can be efficiently suppressed in averaging. In other words, the effect of suppression of the frequency components of a periodic swing per unit measurement time can be improved.

The first position 211 and second position 212 may be pseudo-randomly defined about the position A 210. In this case, because the correlation between the phases of the frequency component of a swing after the conversion step is small (such as substantially 0), the suppression effect of the predetermined frequency component can be increased in averaging the time waveforms of terahertz waves. According to this embodiment, the position A 210 is defined near the center of the adjustment range 213 for the difference in length of the optical paths. However, the present invention is not limited thereto. For example, the position A 210 may be defined at a boundary of the adjustment range 213 for the difference in length of the optical paths.

Figure 6A:
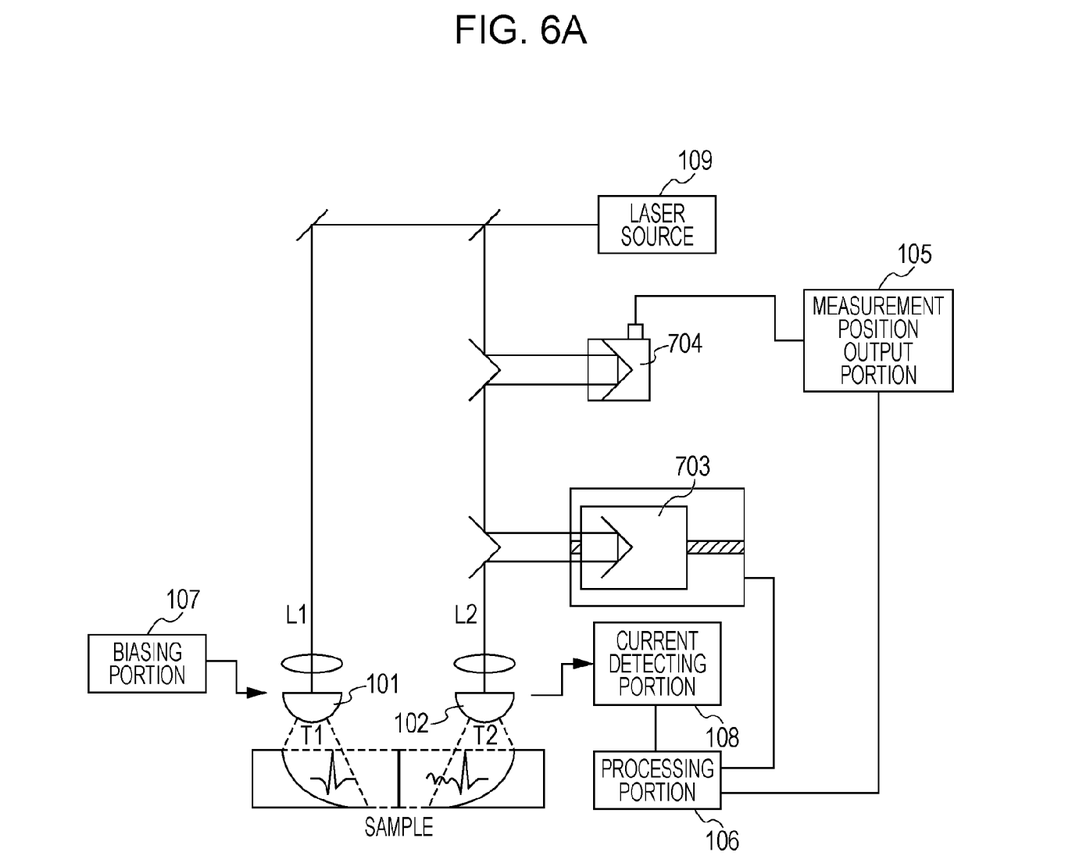
FIG. 6A illustrates another example of the arrangement of a first delay portion and a second delay portion.
Figure 6B:
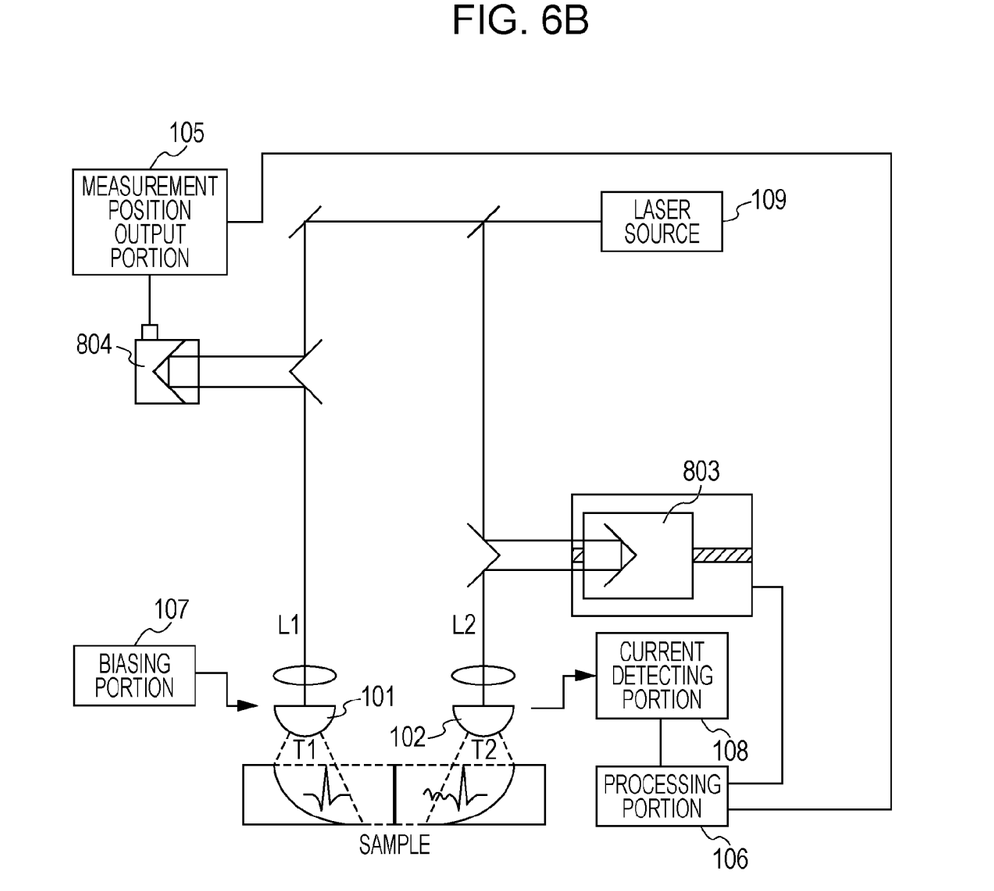
FIG. 6B illustrates another example of the arrangement of a first delay portion and a second delay portion.

According to this embodiment, the second delay optical portion 104 is placed on the first delay optical portion 103. However, the present invention is not limited thereto. For example, as indicated by a first delay optical portion 703 and a second delay optical portion 704 in FIG. 6A, the first delay optical portion 103 and second delay optical portion 104 may be arranged separately on the optical path where the excitation light beam L2 propagates. In this case, the first delay optical portion 103 and second delay optical portion 104 may be arranged separately on the optical path where the excitation light beam L1 propagates. Alternatively, as indicated by a first delay optical portion 803 and a second delay optical portion 804 in FIG. 6B, the first delay optical portion 103 and second delay optical portion 104 may be arranged separately on distinct optical paths where the excitation light beams L2 and L1 propagate respectively. These arrangements can flexibly support various forms and environments of the present apparatus.

The aforementioned configuration allows the terahertz wave measuring apparatus of this embodiment to suppress a frequency component of a periodic swing originating in the form of the first delay optical portion 103. Since the pseudospectrum originating in periodical swinging can be suppressed, the measurement span of the measuring apparatus can be increased, and the analysis performance can be improved.

With reference to drawings, embodiments characterized in an operation flow and others will be described below.

[Second Embodiment]

Figure 3:
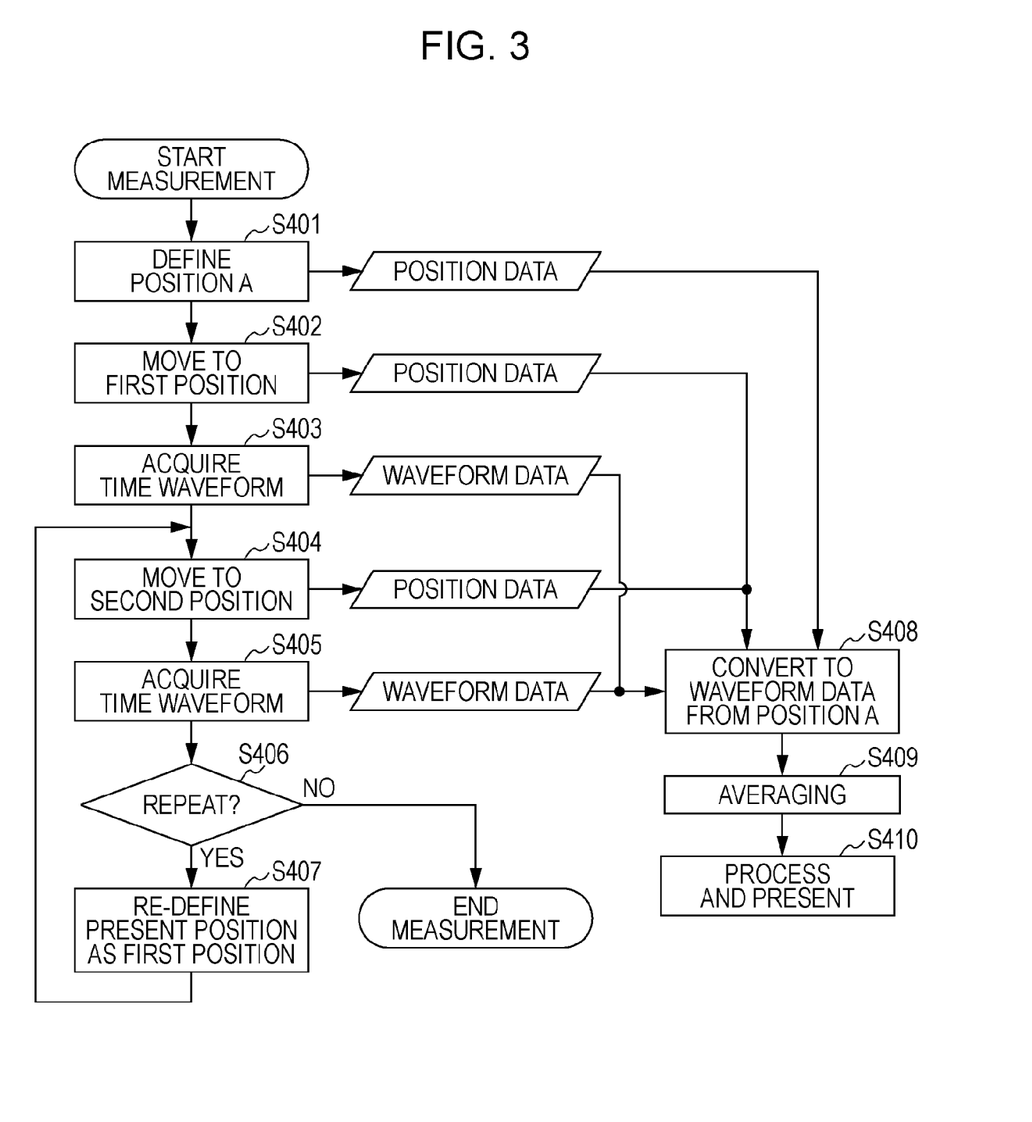
FIG. 3 illustrates an operation flow by a terahertz wave measuring apparatus and method according to a second embodiment of the present invention.

FIG. 3 illustrates an operation flow by a terahertz wave measuring apparatus according to a second embodiment of the present invention. Since the basic configuration of this embodiment is common to that of the first embodiment, the repetitive description will be omitted. Referring to FIG. 3, if the terahertz wave measuring apparatus starts measuring, the processing portion 106 defines the position A 210 (S401). The first delay optical portion 103 is moved to the position A 210, and the first delay optical portion 103 stores the present position data in a storage portion. More specifically, the second delay optical portion 104 is fixed, and the first delay optical portion is moved to the position A. After that, the second delay optical portion 104 is moved every measurement of a time waveform about the position A. The storage portion stores the position data on the delay optical portions at the position A. The storage portion may be provided internally in or externally to the processing portion 106.

Next, the measurement position output portion 105 moves the second delay optical portion 104 to the first position 211 (S402). The measurement position output portion 105 stores the present position data on the second delay optical portion 104 to the storage portion. The second delay optical portion 104 is movable within the adjustment range 213 for the difference in length of the optical paths.

The terahertz wave measuring apparatus at that time moves the sampling point by moving the first delay optical portion 103 to acquire a first terahertz wave time waveform 214 (S403). This is the same operation as in a terahertz wave measuring apparatus in the past. The acquired waveform data include the array of the position of the first delay optical portion 103 and the intensity signal from the current detecting portion 108. The position data corresponds to the time interval of the sampling in the terahertz wave domain. Thus, the data sequence on the position may be converted to a data sequence on a time in the terahertz wave domain. The waveform data on the first terahertz wave time waveform 214 are stored in the storage portion.

The processing portion 106 refers to the storage portion and converts the position data sequence included in the waveform data to the position data sequence at the position A 210 (S408). More specifically, the processing portion 106 refers to the data on the position A 210 and the first position 211 in the storage portion and calculates the difference between the position A 210 and the first position 211. The position data sequence in the waveform data is corrected with the value of the difference. If the position data sequence is a time data sequence, the position data sequence is corrected with the value of the difference converted to the time. The converted waveform data are stored in the storage portion again.

Next, the measurement position output portion 105 moves the second delay optical portion 104 to the second position 212 (S404). The measurement position output portion 105 stores the current position data on the second delay optical portion 104 to the storage portion. The same processing as that on the first position 211 is also performed here (S405 and S408). Thus, for the second terahertz wave time waveform 215, the converted waveform data is stored in the storage portion.

Next, the terahertz wave measuring apparatus monitors the number of times of acquisition of time waveforms to determine whether the number of measurements reaches a predetermined number or not (S406). If the number of measurements is lower than the predetermined number of times, the second position 212 is re-defined to the first position 211, and the processing in steps S404 to S405 is performed (S407). If the number of measurements is equal to or higher than the predetermined number of times, the processing portion 106 refers to a plurality of waveform data pieces stored in the storage portion and averages the time waveforms with the number of measurements (S409). The processing in this step may be performed sequentially every time waveform data is stored in the storage portion, without waiting for the determination in step S406. The averaged waveform data is processed to and presented in a data format requested by an operator (S410). The terahertz wave measuring apparatus ends the measurement upon completion of a series of the steps.

The processing in the steps of this embodiment also provides the same effects as those of the first embodiment.

[Third Embodiment]

Figure 4:
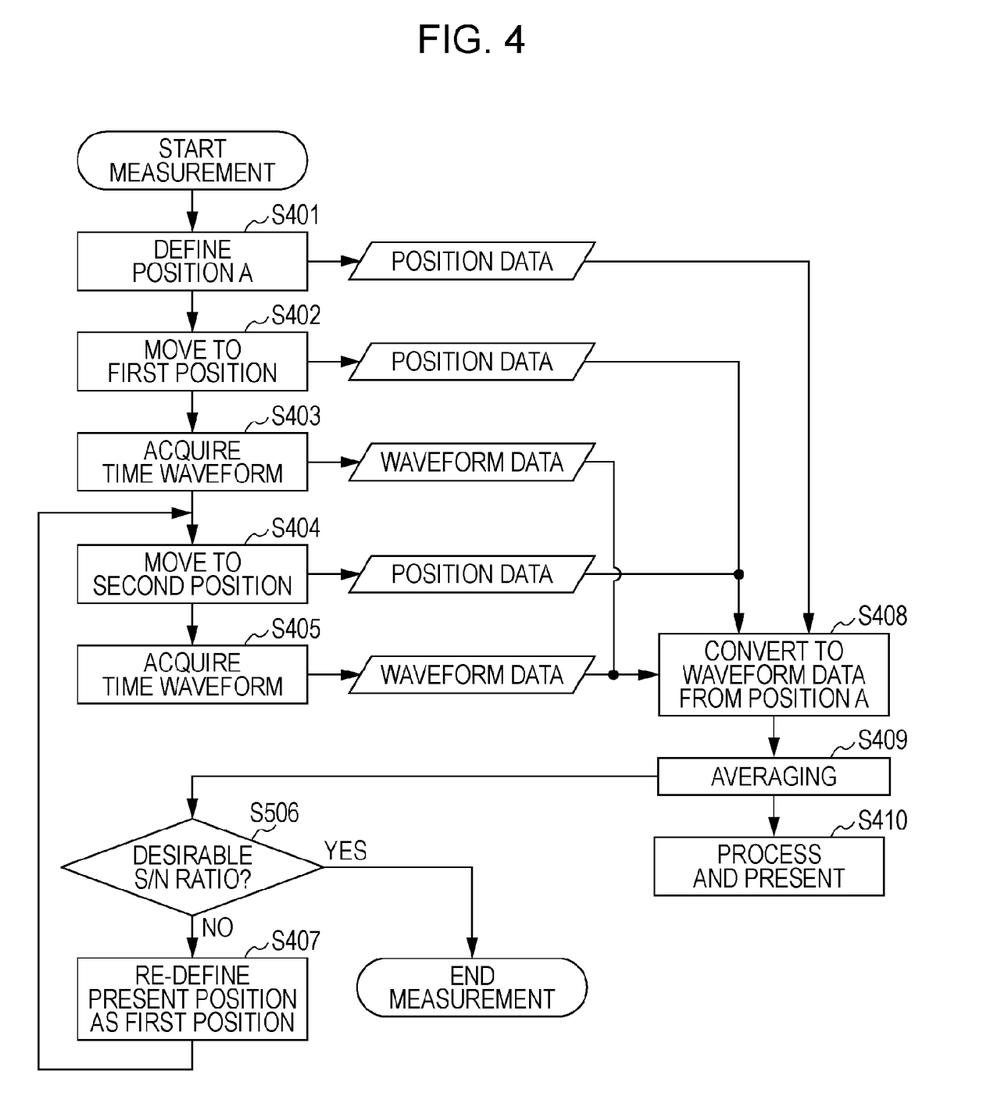
FIG. 4 illustrates an operation flow by a terahertz wave measuring apparatus and method according to a third embodiment of the present invention.

A third embodiment of the present invention relates to a variation example of the operation flow according to the second embodiment. More specifically, the third embodiment is different from the second embodiment in the criterion for determining the completion of the measurement by the terahertz wave measuring apparatus. The repetitive descriptions on those described up to this point will also be omitted. FIG. 4 illustrates an operation flow by the terahertz wave measuring apparatus according to this embodiment. If the terahertz wave measuring apparatus starts measuring, the processing portion 106 defines the position A 210 (S401). The information on the position of the first delay optical portion 103 and the position of the second delay optical portion 104 are stored. Next, the measurement position output portion 105 moves the second delay optical portion 104 to the first position 211 (S402). At this state, the terahertz wave measuring apparatus moves the sampling point by moving the first delay optical portion 103 in a predetermined manner and acquires a first terahertz wave time waveform 214 (S403). Next, the processing portion 106 refers to the information stored in the storage portion and converts the position data sequence included in the waveform data to the position data sequence at the position A 210 (S408). Next, the measurement position output portion 105 moves the second delay optical portion 104 to the second position 212 (S404). At this state, the terahertz wave measuring apparatus moves the sampling point by moving the first delay optical portion 103 in a predetermined manner and acquires a second terahertz wave time waveform 215 (S405). The processing portion 106 here also refers to the information in the storage portion and converts the position data sequence included in the waveform data to the position data sequence at the position A 210 (S408).

According to this embodiment, when the second terahertz wave time waveform 215 is measured, the time waveforms are averaged sequentially (S409). After that, the terahertz wave measuring apparatus calculates the SN ratio of the averaged time waveform of terahertz waves and determines whether a desirable SN ratio has been acquired or not (S506). If the time waveform does not have the desirable SN ratio, the terahertz wave measuring apparatus re-defines the second position 212 to the first position 211 and performs the processing in steps S404 to S409 (S407). If the time waveform has the desirable SN ratio, the terahertz wave measuring apparatus stops the repetition of the measurement. The averaged waveform data are processed to and presented in a data format requested by an operator (S410). The terahertz wave measuring apparatus ends the measuring upon completion of the series of steps.

Performing these steps of this embodiment allows the terahertz wave measuring apparatus to end the measurement when the desirable SN ratio is obtained. Thus, the apparatus can typically provide a time waveform with the same SN ratio. Therefore, the precision of the comparison between a plurality of time waveforms can be improved. Since the measurement ends when the desirable SN ratio is obtained, no unnecessary measurement is performed, and the working efficiency can be improved.

[Fourth Embodiment]

Figure 5:
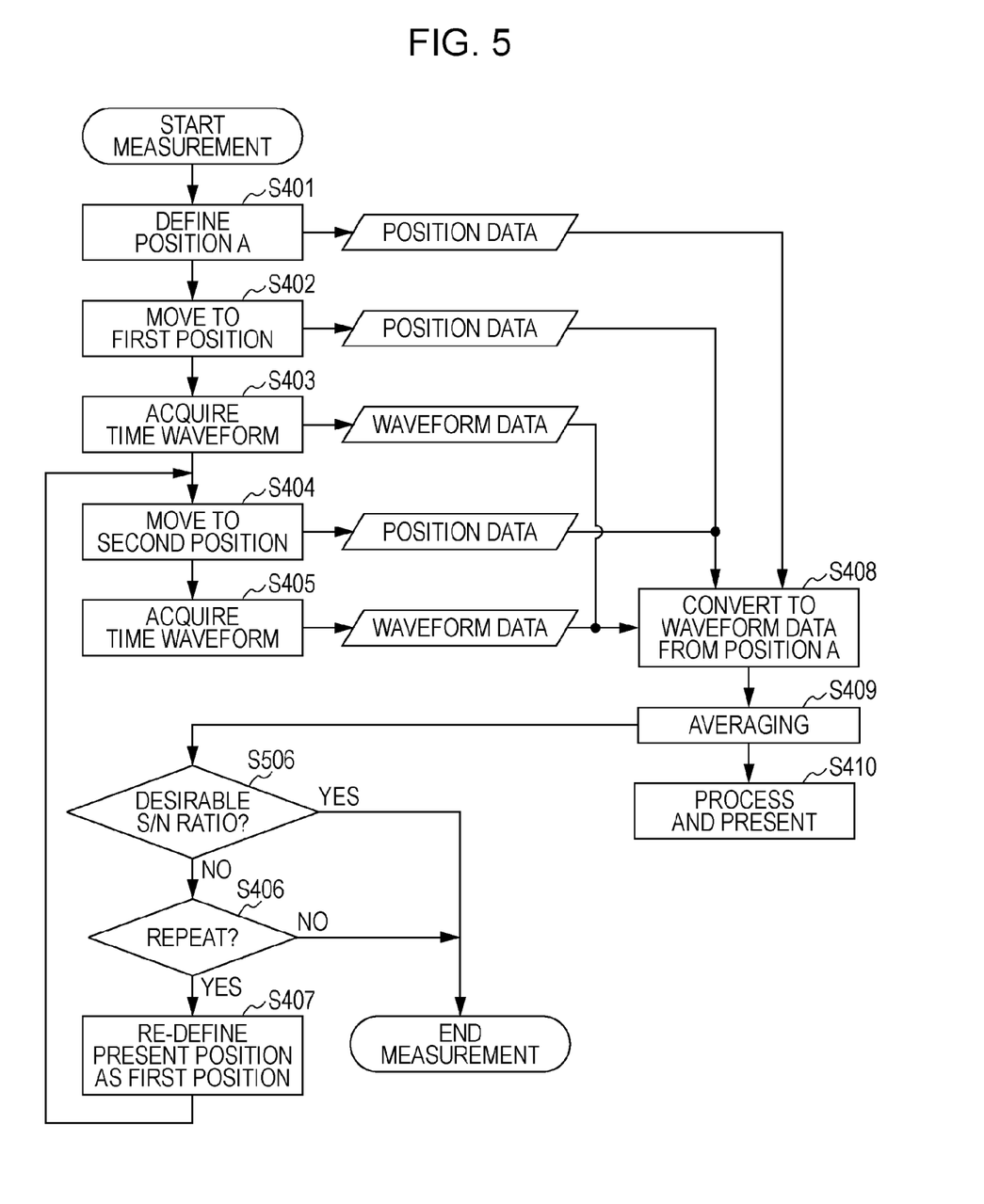
FIG. 5 illustrates an operation flow by a terahertz wave measuring apparatus and method according to a fourth embodiment of the present invention.

A fourth embodiment of the present invention relates to a variation example of the operation flow according to the third embodiment. More specifically, the fourth embodiment is different from the third embodiment in the criterion for determining the completion of the measurement by the terahertz wave measuring apparatus. The repetitive descriptions on those described up to this point will also be omitted. FIG. 5 illustrates an operation flow by the terahertz wave measuring apparatus according to this embodiment. If the terahertz wave measuring apparatus starts measuring, the processing portion 106 defines the position A 210 (S401). The measurement position output portion 105 moves the second delay optical portion 104 to the first position 211 (S402). The terahertz wave measuring apparatus moves the sampling point by moving the first delay optical portion 103 in a predetermined manner and acquires a first terahertz wave time waveform 214 (S403). The processing portion 106 refers to the information in the storage portion and converts the position data sequence included in the waveform data to the position data sequence at the position A 210 (S408). The measurement position output portion 105 moves the second delay optical portion 104 to the second position 212 (S404). The terahertz wave measuring apparatus moves the sampling point by moving the first delay optical portion 103 and acquires a second terahertz wave time waveform 215 (S405). The processing portion 106 refers to the information in the storage portion and converts the position data sequence included in the waveform data to the position data sequence at the position A 210 (S408).

According to this embodiment, when the second time waveforms 215 of terahertz waves are measured, the time waveforms are averaged sequentially (S409). The terahertz wave measuring apparatus calculates the SN ratio of the averaged time waveform of terahertz wave and determines whether a desirable SN ratio has been acquired or not (S506). The terahertz wave measuring apparatus further monitors the number of measurements of time waveforms and determines whether the number of measurements reaches a predetermined number or not (S406). If the SN ratio of the time waveform does not reach a desirable SN ratio and the number of measurements does not reach the predetermined number of times, the terahertz wave measuring apparatus re-defines the second position 212 to the first position 211 and performs the processing in steps S404 to S409 (S407).

If the time waveform has the desirable SN ratio or the number of measurements reaches the predetermined number, the terahertz wave measuring apparatus stops the repetition of the measurement. The averaged waveform data are processed to and presented in a data format requested by an operator (S410). The terahertz wave measuring apparatus ends the measuring upon the completion of the series of steps.

The processing in those steps of this embodiment allows the terahertz wave measuring apparatus to complete the measurement within a predetermined period of time even when a desirable SN ratio is difficult to obtain for some reason. According to this embodiment, a plurality of conditions for ending the measurement may be prepared to increase the general versatility. More specifically, for example, excessively long measurement time can be prevented, and the stress on the measurement staff can be reduced. Furthermore, unexpected circumstances can also be easily addressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-135631, filed Jun. 5, 2009, which is hereby incorporated by reference herein in its entirety.

What is claimed is:

1. A method for acquiring an accurate time waveform of terahertz waves using an apparatus including a generating portion which generates terahertz waves, a detecting portion which detects the terahertz waves, a first delay portion which changes a difference in length of the optical paths of excitation light beams radiated to the generating portion and the detecting portion, and a second delay portion which changes a difference between times taken for the excitation light beams to reach the generating portion and to reach the detecting portion, the method comprising:

acquiring a first time waveform by using the first delay portion with a first difference in length of the optical paths;

using the second delay portion to change the first difference in length of the optical paths to a second difference in length of the optical paths that is different from the first difference in length of the optical paths;

acquiring a second time waveform by using the first delay portion with the second difference in length of the optical paths;

adjusting the acquired first and second time waveforms in accordance with a predetermined difference in length of the optical paths based on the first and second differences in length of the optical paths; and averaging the first and second time waveforms according to the predetermined differences in length of the optical paths to supply the accurate time waveform.

2. The method according to claim 1, further comprising:

radiating terahertz waves generated by the generating portion to a sample;

detecting terahertz waves passed through or reflected by the sample by using the detecting portion; and acquiring information on the sample by using the accurate time waveform having a frequency component originating in the movement of the first delay portion and suppressed by the averaging.

3. An apparatus which acquires an accurate time waveform of terahertz waves, the apparatus comprising:

a generating portion which generates terahertz waves;

a detecting portion which detects terahertz waves generated by the generating portion;

a first delay portion which changes the difference in length of the optical paths of the excitation light beams radiated to the generating portion and the detecting portion;

a second delay portion which changes the difference between times taken for the excitation light beams to reach the generating portion to reach and the detecting portion; and a processing portion which acquires first and second time waveforms by using the first delay portion with first and second differences in length of the optical paths in the second delay portion, wherein, to supply the accurate time waveform, the processing portion adjusts the acquired first and second time waveforms in accordance with a predetermined difference in length of the optical paths based on the first and second differences in length of the optical paths and averages the first and second time waveforms according to the predetermined difference in length of the optical paths.

4. The apparatus according to claim 3, wherein:

terahertz waves generated by the generating portion are radiated to a sample;

terahertz waves passed through or reflected by the sample are detected by the detecting portion; and information on the sample is acquired by using the accurate time waveform having a frequency component originating in the movement of the first delay portion but suppressed by the averaging.

* * * * *